United States Patent [19]

Friedman

[11] Patent Number: 4,479,953
[45] Date of Patent: Oct. 30, 1984

[54] PYRAZINE ALDIMINE COMPOUNDS AS ANTIMICROBIAL AGENTS

[75] Inventor: Arthur J. Friedman, Marlboro, N.J.

[73] Assignee: Merck & Co., Inc., Rahway, N.J.

[21] Appl. No.: 526,306

[22] Filed: Aug. 25, 1983

[51] Int. Cl.³ .................... C07D 241/02; A01N 43/60
[52] U.S. Cl. .................................... 424/250; 544/409
[58] Field of Search ......................... 544/409; 424/250

[56] References Cited

U.S. PATENT DOCUMENTS 3,274,192  9/1966  Cragoe et al. ..................... 544/409
3,299,063  1/1967  Cragoe et al. ..................... 544/409
3,341,540  9/1967  Cragoe et al. ..................... 544/409
3,487,082 12/1969  Cragoe et al. ..................... 544/409
4,442,095  4/1984  Johnston ............................ 544/409

Primary Examiner—Donald G. Daus
Assistant Examiner—William A. Teoli, Jr.
Attorney, Agent, or Firm—Mario A. Monaco; Alice O. Robertson; R. Brent Olson

[57] ABSTRACT

The instant invention is directed to a pyrazine compound represented by the formula

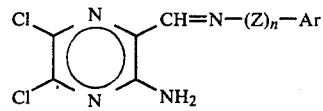

wherein
Z is —NH—, —NHSO$_2$—, —NHCO— or —S—,
Ar is a phenyl ring substituted by 1 or 2 substituents selected from the group consisting of halo, lower alkyl, lower alkoxy or nitro, and
n is 0 or 1.

9 Claims, No Drawings

PYRAZINE ALDIMINE COMPOUNDS AS ANTIMICROBIAL AGENTS

DESCRIPTION OF THE INVENTION

The present invention is directed to aldimine compounds represented by the formula:

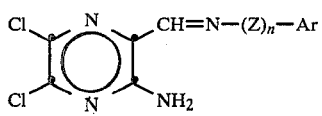  I

In this and succeeding formulas:
Z is —NH—, —NHSO$_2$—, —NHCO— or —S—,
Ar is phenyl or substituted phenyl, and
n is 0 or 1.

By "substituted phenyl" is meant that the phenyl ring has one or more substituents selected from halo, alkyl, alkoxy or nitro. Preferably, it is a mono substituted group, although especially with smaller groups it may be polysubstituted.

The products of the present invention are usually high-melting solids which often decompose at the melting point. They are difficultly soluble both in water and in organic solvents.

The compounds of the present invention are antimicrobial agents, particularly useful for the control of fungi. In the control of fungal organisms, the compounds show an especially high degree of control against the genus Alternaria.

The compounds of the present invention may be prepared by reacting 3-amino-5,6-dichloropyrazinealdehyde represented by the formula:

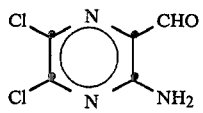  II with a basic aromatic compound represented by the formula:

H$_2$N—(Z)$_n$—Ar   III to produce the desired pyrazine aldimine compound of Formula I and water by-product. The reactants may be brought together in a polar inert inorganic solvent. Suitable solvents are alcohols, especially ethanol and isopropanol. The exact amounts of the reactants are not critical, some of the desired product being obtained when any proportion of the ingredients are employed; however, good results are obtained when employing substantially equimolar proportions of 3-amino-5,6-dichloropyrazinaldehyde and a basic aromatic compound of Formula III. The reaction may be carried out at ambient temperature to about 100° C. It is conveniently carried out at the reflux temperature of the solvent. The reaction is rapid, generally instantaneous and is complete within a few minutes to an hour with a solid product precipitating in the reaction mixture and the by-product water dissolving in the alcohol or polar solvent. After completion of the product formation, the product may be removed from the reaction mixture by filtration. The product may be purified, if desired, by recrystallization from an alcohol or other polar solvent.

The reactant 3-amino-5,6-dichloropyrazinealdehyde of Formula II may be prepared by reducing 2-amino-5,6-dichloro-3-(methoxycarbonyl)pyrazine to 2-amino-5,6-dichloro-3-(hydroxymethyl)-pyrazine which then is oxidized to the aldehyde. The reduction may be carried out by contacting a solution of the ester in an inert solvent such as tetrahydrofuran with potassium borohydride and lithium chloride at ambient temperature, preferably overnight and thereafter diluting with water and cooling to obtain the hydroxymethyl compound. The hydroxymethyl compound is then reacted with activated manganese dioxide in a solvent such as acetone to obtain the desired aldehyde starting material which may be isolated by removing the manganese dioxide, diluting with water to precipitate the aldehyde and isolating by conventional procedures.

The basic aromatic compound represented by Formula III may be obtained commercially when Ar is phenyl and may be conveniently synthesized from commercially available starting materials when Ar is substituted phenyl as hereinafter described.

When n in Formula III is 0, the compound is related to aniline and may be represented by Formula IV:

   IV

Most are available commercially, others are readily prepared by a number of methods familiar to those skilled in the art.

When in Formula III, Z is —NH— and n is 1, the compound is a phenylhydrazine derivation which may be represented by Formula V:

   V

A number of phenylhydrazine compounds are available commercially either as a free base or as a hydrochloride salt. They also may be synthesized readily by a number of methods known to those skilled in the art. Thus, for example, an appropriately substituted aniline in a mixture of a concentrated hydrochloric acid and water may be cooled to 0° to obtain hydrochloride of the substituted aniline and then diazotized and reduced by conventional methods to obtain the desired substituted phenylhydrazine. When the substituent or substituents on the phenyl ring are of the kind to render a halogen substituent on the phenyl ring labile, the appropriately substituted halobenzene may be reacted with hydrazine to obtain the desired substituted phenylhydrazine compound. Thus, for example, 2,4-dinitro-1-chlorobenzene may be reacted with hydrazine to obtain 2,4-dinitrophenylhydrazine. Suitable conditions may be found in standard texts and references on synthetic procedures such as, for example, Vogel, "A Textbook of Practical Organic Chemistry" Longmans L. Green and Company, pp. 607–611.

When the basic aromatic compound is one in which Z in Formula III is —NHSO$_2$—, it may be prepared from the corresponding appropriately substituted benzenesulfonyl chloride and hydrazine preferably in an inert solvent such as methylene chloride. In the preparation, it is desirable to add the appropriately substituted benzenesulfonyl chloride in an inert solvent such as methylene chloride dropwise to hydrazine also in an inert solvent, the hydrazine being present in molar excess to take up the by-product hydrogen chloride. The hydrazine reactant is represented by Formula VI:

H$_2$NNHSO$_2$Ar 

When the basic aromatic compound is one in which Z in Formula III is —NHCO—, it may be represented by Formula VII:

H$_2$NNHCOAr 

The compound of Formula VII may be prepared in a manner very similar to that described for the preparation of the compound of Formula VI except that the appropriate aromatic carboxylic acid chloride is employed instead of the aromatic sulfonic acid chloride.

When the aromatic compound is such that Z in Formula III is —S— so that it is a sulfenamide, it may be represented by Formula VIII.

H$_2$NSAr 

The sulfenamide may be prepared by the reaction of substituted benzenesulfenyl chloride with ammonia or ammonium hydroxide. The benzenesulfenyl chloride in turn may be readily prepared from readily available substituted benzenethiol or substituted phenyl disulfide. In such preparation, the substituted benzenethiol or substituted phenyl disulfide is dissolved in carbon tetrachloride and chlorine added thereto either as a solution in carbon tetrachloride or as gaseous chlorine bubbled into the solution, whereupon a reaction takes place with the formation of benzenesulfenyl chloride and hydrogen chloride by-product. The reaction is carried out with cooling at about 0° C. and after completion of the addition, the hydrogen chloride by-product is removed under reduced pressure. The resulting sulfenyl chloride, if solid, may be recrystallized and if liquid, may be distilled to obtain the purified intermediate material.

The resulting sulfenyl chloride may then be employed to prepare the substituted benzenesulfenamide. Preparation of the sulfenamide may be carried out by adding ammonium hydroxide to a solution of the sulfenyl chloride in an inert solvent such as carbon tetrachloride and stirring for a short time whereupon the desired substituted benzenesulfenamide precipitates in the reaction mixture and may be recovered by filtration and purified, if desired, by recrystallization.

In carrying out the preparation of the desired pyrazine aldimine compound of Formula I, 3-amino-5,6-dichloropyrazinaldehyde and the appropriate basic aromatic compound of Formula II are mixed together in ethanol or other alcohol and warmed to the reflux temperature of the solvent and maintained at this temperature for from a few minutes to about an hour whereupon a reaction takes place with the formation of the desired pyrazine aldimine compound which precipitates in the reaction mixture. The pyrazine aldimine compound may be recovered by filtration and purified by recrystallization from an appropriate solvent such as ethanol or other alcohol.

The following examples illustrate the invention but are not to be construed as limiting.

EXAMPLE 1

5,6-Dichloro-3-[(2-phenylhydrazono)methyl]pyrazinamine

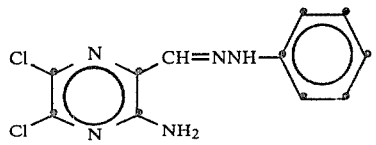

0.96 gram (0.005 mole) of 3-amino-5,6-dichloropyrazinaldehyde, 0.54 gram (0.005 mole) of phenylhydrazine and 20 milliliters of ethanol were heated with stirring and refluxed for 10 minutes to obtain a 5,6-dichloro-3-[(2-phenylhydrazono)methyl]pyrazinamine product as a solid. The reaction mixture was allowed to cool and the solid product recovered by filtration and recrystallized from ethanol to obtain 0.71 gram (50 percent yield) of purified product as yellow flakes, m.p. 277°–278° C. (dec.). Elemental analyses were as follows:

Calc'd for C$_{11}$H$_9$Cl$_2$N$_5$ (m.w. 282.13): C, 46.83; H, 3.22; N, 24.82. Found: C, 46.85; H, 3.15; N, 24.90.

EXAMPLE 2

In a similar manner, the following compounds are prepared:

5,6-Dichloro-3-[2-(2,4-dinitrophenyl)hydrazono]methylpyrazinamine from 3-amino-5,6-dichloropyrazinaldehyde and 2,4-dinitrophenylhydrazine.

5,6-Dichloro-3-[2-(p-nitrophenyl)hydrazono]methyl pyrazinamine from 3-amino-5,6-dichloropyrazinaldehyde and p-nitrophenylhydrazine.

5,6-Dichloro-3-[2-(m-tolyl)hydrazono]methylpyrazinamine from 3-amino-5,6-dichloropyrazinaldehyde and m-tolylhydrazine.

5,6-Dichloro-3-[2-(o-chlorophenyl)hydrazono]methylpyrazinamine from 3-amino-5,6-dichloropyrazinaldehyde and o-chlorophenylhydrazine.

EXAMPLE 3

Benzenesulfonic Acid, 2-[(3-amino-5,6-dichloropyrazinyl)methylene]hydrazide

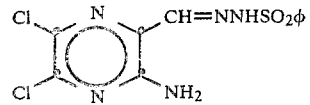

In a similar manner, 0.96 gram (0.005 mole) of 3-amino-5,6-dichloropyrazinaldehyde, 0.86 gram (0.005 mole) of benzenesulfonylhydrazine and 50 milliliters of ethanol were stirred together with heating under reflux to obtain a benzenesulfonic acid 2-[(3-amino-5,6-chloropyrazinyl)methylene]hydrazide product which precipitated in the reaction mixture. The product was recovered by filtration and recrystallized from ethanol to obtain 0.75 gram of purified product having a lemon yellow color and a melting point of 242°–243° C. (dec). Elemental analyses were as follows:

Calc'd for C$_{11}$H$_9$Cl$_2$N$_5$O$_2$S (m.w. 346.20): C, 38.16; H, 2.62; N, 20.23. Found: C, 37.38; H, 2.48; N, 21.05.

EXAMPLE 4

Benzoic Acid, 2-[(3-amino-5,6-dichloropyrazinyl)methylene]hydrazide

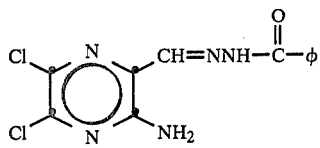

In a similar manner, 0.96 gram (0.005 mole) of 3-amino-5,6-dichloropyrazinaldehyde, 0.08 gram (0.005 mole) of benzoic hydrazide and 100 milliliters of ethanol were mixed together and refluxed for 10 minutes to obtain a benzoic acid 2-[(3-amino-5,6-dichloropyrazinyl)methylene]hydrazide product. The product was recovered and recrystallized three times from ethanol to obtain yellow crystals which after drying 2 hours at 100° C. had the following elemental analyses.

Calc'd for $C_{12}H_9Cl_2N_5O$ (m.w. 310.14): C, 46.47; H, 2.93; N, 22.58. Found: C, 47.25; H, 2.74; N, 23.22.

EXAMPLE 5

5,6-Dichloro-3-[(2-nitrophenyl)thioimino]methylpyrazinamine

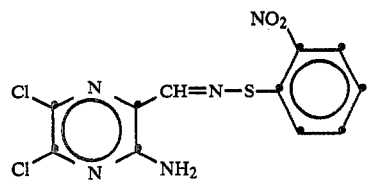

Preparation of o-nitrobenzenesulfenamide 50 grams of o-nitrobenzenesulfenyl chloride was added to carbon tetrachloride with stirring, followed by 50 milliliters of ammonium hydroxide over a one-minute period. The stirring was continued over 5 minutes to obtain an o-nitrobenzenesulfenamide intermediate which precipitated in the reaction mixture. The o-nitrobenzenesulfenamide intermediate was recovered by filtration and dried.

Preparation of 5,6-dichloro-3-[(2-nitrophenylthioimino]methylpyrazinamine 0.76 gram (0.005 mole) of 3-amino-5,6-dichloropyrazinaldehyde was dissolved in 50 milliliters of hot ethanol and poured into a solution of 0.85 gram (0.005 mole) of o-nitrobenzenesulfenamide prepared as above described. To the resulting mixture, 0.25 gram (0.005 mole) of ammonium chloride was added and the reaction mixture heated with stirring and refluxed for about 5 minutes whereupon the desired 3,5-dichloro-3-[(2-nitrophenyl)thioimino]methylpyrazinamine product began to precipitate as a yellow solid. After completion of the heating, the reaction mixture was allowed to cool, the product filtered and recrystallized from ethanol to obtain 0.35 gram of purified product, m.p. 235°–236° C. Elemental analyses of the product were as follows:

Calc'd for $C_{11}H_7Cl_2N_3OS$ (m.w. 300.16): C, 38.39; H, 2.05; N, 20.35. Found: C, 38.24; H, 2.06; N, 20.06.

EXAMPLE 6

In a similar manner to that described in Example 3, the following compounds are prepared:

p-Toluenesulfonic acid 2-[(3-amino-5,6-dichloropyrazinyl)methylene]hydrazide by the reaction of p-toluenesulfonyl chloride with hydrazine in tetrahydrofuran to form p-toluenesulfonylhydrazine, followed by the reaction of the latter with 3-amino-5,6-dichloropyrazinaldehyde.

p-Chlorobenzenesulfonic acid 2-[(3-amino-5,6-dichloropyrazinyl)methylene]hydrazide by the reaction of p-chlorobenzenesulfonyl chloride with hydrazine to form p-chlorobenzenesulfonylhydrazine, followed by the reaction of the latter with 3-amino-5,6-dichloropyrazinaldehyde.

p-Bromobenzenesulfonic acid 2-[(3-amino-5,6-dichloropyrazinyl)methylene]hydrazide by the reaction of p-bromobenzenesulfonyl chloride with hydrazine to form p-bromobenzenesulfonylhydrazine, followed by the reaction of the latter with 3-amino-5,6-dichloropyrazinaldehyde.

EXAMPLE 7

In a manner similar to that described in Example 4, the following compounds are prepared:

p-Bromobenzoic acid 2-[(3-amino-5,6-dichloropyrazinyl)methylene]hydrazide by the reaction of p-bromobenzoyl chloride with hydrazine to form p-bromobenzoylhydrazine, followed by the reaction of the latter with 3-amino-5,6-dichloropyrazinaldehyde.

p-Chlorobenzoic acid 2-[(3-amino-5,6-dichloropyrazinyl)methylene]hydrazide by the reaction of p-chlorobenzoyl chloride with hydrazine to form p-chlorobenzoylhydrazine, followed by the reaction of the latter with 3-amino-5,6-dichloropyrazinaldehyde.

3,5-Dinitrobenzoic acid 2-[(3-amino-5,6-dichloropyrazinyl)methylene]hydrazide by the reaction of 3,5-dinitrobenzoyl chloride with hydrazine to form 3,5-dinitrobenzoylhydrazine, followed by the reaction of the latter with 3-amino-5,6-dichloropyrazinaldehyde.

EXAMPLE 8

In a manner similar to that described in Example 5, the following compounds are prepared:

5,6-Dichloro-3-[(2,4-dinitrophenyl)thioimino]methylpyrazinamine by the reaction of 2,4-dinitrobenzenesulfenyl chloride with ammonium hydroxide to form 2,4-dinitrobenzenesulfenamide, followed by reaction of the latter with 3-amino-5,6-dichloropyrazinaldehyde.

5,6-Dichloro-3-[(o-chlorophenyl)thioimino]methylpyrazinamine by the reaction of o-chlorobenzenesulfenyl chloride with ammonium hydroxide to form o-chlorobenzenesulfenamide, followed by reaction of the latter with 3-amino-5,6-dichloropyrazinealdehyde.

EXAMPLE 9

5,6-Dichloro-3-[(4-chlorophenyl)imino]methyl-pyrazinamine

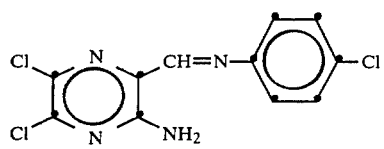

1.92 grams (0.01 mole) of 3-amino-5,6-dichloropyrazinaldehyde, 1.28 grams (0.01 mole) of p-chloroaniline and 25 milliliters of ethanol were stirred together, heated and refluxed for 5 minutes whereupon a reaction took place with the formation of a 5,6-dichloro-3-[(4-chlorophenyl)imino]methylpyrazinamine product which precipitated in the reaction mixture. The reaction mixture was allowed to cool and the solid product recovered by filtration and recrystallized from ethanol to obtain a purified product, m.p. 179°–182° C. in a yield of 2.5 grams (83 percent of theory). The product had elemental analyses as follows:

Calc'd for $C_{11}H_7Cl_3N_4$ (m.w. 301.56): C, 43.81; H, 2.34; N, 18.58. Found: C, 43.70; H, 2.24; N, 18.62.

EXAMPLE 10

5,6-Dichloro-3-[(4-methoxyphenyl)imino]methylpyrazinamine

In a manner similar to that described in Example 9, 1.92 grams (0.01 mole) of 3-amino-5,6-dichloropyrazinaldehyde, 1.23 g (0.01 mole) of p-anisidine and 15 milliliters of ethanol were mixed together and heated at reflux temperature to obtain a 5,6-dichloro-3-[(4-methoxyphenyl)imino]methylpyrazinamine product which precipitated in the reaction mixture. The product was recovered by filtration, recrystallized from ethanol to obtain 2.14 grams of a purified product, m.p. 167°–168° C. (dec). Elemental analyses were as follows:

Calc'd for $C_{12}H_{10}CL_2N_4O$ (m.w. 297.14): C, 48.51; H, 3.39; N, 18.75. Found: C, 48.47; H, 3.41; N, 18.92.

EXAMPLE 11

In a manner similar to that described in Examples 9 and 10, the following compounds are prepared:

5,6-Dichloro-3-[(2-methoxyphenyl)imino]methyl-pyrazineamine from 3-amino-5,6-dichloropyrazinaldehyde and o-anisidine.

5,6-Dichloro-3-[(p-tolyl)imino]methylpyrazinamine from 3-amino-5,6-dichloropyrazinaldehyde and p-toluidine.

5,6-Dichloro-3-[(4-t-butylphenyl)imino]methyl-pyrazinamine from 3-amino-5,6-dichloropyrazinaldehyde and 4-t-butylaniline.

5,6-Dichloro-3-[(3-nitrophenyl)imino]methylpyrazinamine from 3-amino-5,6-dichloropyrazinaldehyde and 3-nitroaniline.

5,6-Dichloro-3-[(4-ethylphenyl)imino]methylpyrazinamine from 3-amino-5,6-dichloropyrazinaldehyde and p-phenetidine.

The pyrazinaldimine compounds have antimicrobial properties, especially against fungi. They are adaptable to being incorporated into paint, film, and coating compositions for protection against attack by fungal organisms.

The antifungal properties were discovered in a test which is carried out in the following manner:

A stock solution of a compound to be tested for antimicrobial activity is prepared in 25% methanol. Dilutions of the stock solution are made into Sabouraud maltose agar, and the agar poured into sterile petri dishes. After hardening, the plates are streaked with an aqueous suspension of the test organism. The inoculated plates are incubated at about 30° C. and the readings made after 4 to 5 days' incubation to determine fungal growth. The lowest concentration that inhibits fungal growth is recorded as minimum inhibitory concentration. The results showing antifungal activity may be seen in the following table:

TABLE 1

| Compound | Minimum Inhibitory Concentration (ppm) | | | |
|---|---|---|---|---|
| | Aspergillus niger | Pullularia pullulens | Penicillum funiculosum | Alternaria brassicicola |
| 5,6-Dichloro-3-[(4-chlorophenyl)imino]-methyl-pyrazinamine | 200 | 100 | 200/200 | 50/100 |
| 5,6-Dichloro-3-[(4-methoxyphenyl)imino]-methyl-pyrazinamine | 200 | 50 | 100 | 50 |
| 5,6-Dichloro-3-[(2-phenyl-hydrazono)-methyl-pyrazinamine | >200 400/750 | >200 400 | >200 400/750 | >200 400 |
| Benzene-sulfonic acid, 2-[(3-amino-5,6-dichloro-pyrazinyl)methylene]-hydrazide | >200 1000/1000 | >200 750 | >200 1000/1000 | >200 750 |
| Benzoic acid, 2-[(3-amino-5,6-dichloro-pyrazinyl)methylene]-hydrazide | 1000 | 200 | 750 | 50 |
| 5,6-Dichloro-3-[(2-nitrophenyl)thio-imino]-methyl-pyrazinamine | 1000 | 400/750 | 400/750 | 100 |

In employing the pyrazine aldimine compounds of the present invention for antimicrobial control, compositions containing said pyrazine aldimine compounds may be prepared in a liquid, solid or aerosol inert carrier to be applied to the substrate or area where antimicrobial control is desired. Such compositions may contain the pyrazine aldehyde compounds in an amount of from about 0.1 percent to 10 percent by weight, or if concentrate composition up to 95 percent by weight. Inert carriers include liquids such as petroleum distillates, kerosene, aromatic hydrocarbons and the like, and finely divided solids such as surface active agents, clays, diatomaceous earth, bentonite, mahogany soaps, talc, attapulgite and the like. Solid carriers which have surface active properties are useful also for preparing emulsions and dispersions. The compositions may be diluted or employed without modification to provide an antimicrobially effective amount of the pyrazine aldimine compound in the substrate or area to be controlled of at least about 50 parts per million by weight and up to 10,000 parts per million or more, depending on the organism and substrate.

Preparation of Starting Material
3-Amino-5,6-dichloropyrazinaldehyde

A. 2-Amino-5,6-dichloro-3-(hydroxymethyl)pyrazine 88 grams of 2-amino-5,6-dichloro-3-(methoxycarbonyl)pyrazine, 27 grams of potassium borohydride, 21 grams of lithium chloride were added to 700 milliliters of tetrahydrofuran and the reaction mixture stirred for 18 hours to obtain 2-amino-5,6-dichloro-3-hydroxymethylaldehyde in the reaction mixture. The mixture was diluted with 2000 milliliters of water and chilled to obtain 2-amino-5,6-dichloro-3-(hydroxymethyl)pyrazine, m.p. 174°–176° C.

B. 3-Amino-5,6-dichloropyrazinaldehyde 3.9 grams of 2-amino-5,6-dichloro-3-(hydroxymethyl)pyrazine, prepared as above described and 12.0 grams of activated manganese dioxide were placed in 120 milliliters of acetone and the mixture stirred at ambient temperature for about 2.5 hours. At the end of this time the spent and excess manganese dioxide was filtered off, the filtrate concentrated to about 60 milliliters, 60 milliliters of water added to the concentrated filtrate and resulting mixture cooled to precipitate 3-amino-5,6-dichloropyrazinealdehyde, m.p. 147°–150° C.

The 2-amino-5,6-dichloro-3-(methoxycarbonyl)pyrazine (also named methyl 3-amino-5,6-dichloropyrazinecarboxylate) may be prepared by a method described in J. Med. Chem. 10, 66 (1967), from 2-amino-3-carbomethoxypyrazine, reported in J. Am. Chem. Soc. 67, 1711 (1945), which in turn is prepared from lumazine whose preparation from readily available materials is reported in J. Am. Chem. Soc. 67, 802 (1945).

What is claimed is:

1. A pyrazine compound represented by the formula:

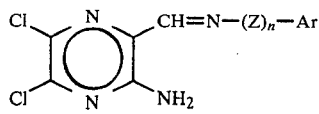

wherein
Z is —NH—, —NHSO$_2$—, —NHCO— or —S—,
Ar is phenyl or a phenyl ring substituted by 1 or 2 substituents selected from the group consisting of halo, lower alkyl, lower alkoxy or nitro, and
n is 0 or 1.

2. A compound according to claim 1 which is 5,6-dichloro-3-[(2-phenylhydrazono)methyl]pyrazinamine.

3. A compound according to claim 1 which is benzenesulfonic acid 2-[(3-amino-5,6-dichloropyrazinyl)-methylene]hydrazide.

4. A compound according to claim 1 which is benzoic acid, 2-[(3-amino-5,6-dichloropyrazinyl) methylene]hydrazide.

5. A compound according to claim 1 which is 5,6-dichloro-3- [(2-nitrophenyl)thioimino]methylpyrazinamine 6. A compound according to claim 1 which is 5,6-dichloro-3- [(4-chlorophenyl)imino]methylpyrazinamine.

7. A compound according to claim 1 which is 5,6-dichloro-3- [(4-methoxyphenyl)imino]methylpyrazinamine.

8. An antimicrobial composition comprising an inert carrier and an antimicrobially effective amount of a compound of claim 1.

9. A method for inhibiting microbial growth which comprises applying an antimicrobially effective amount of a compound of claim 1.

* * * * *